(12) United States Patent
Cebollero et al.

(10) Patent No.: US 6,376,792 B1
(45) Date of Patent: Apr. 23, 2002

(54) METHOD AND APPARATUS FOR INDIVIDUAL DESTRUCTION OF SYRINGE NEEDLES BY MELTING UNDER THE EFFECT OF ELECTRIC CURRENT

(75) Inventors: Jean Cebollero, Oloron Sainte Marie; Fabrice Bounaix; Bruno Golliard, both of Luneville; Jacques Marcandelli, Foulcrey, all of (FR)

(73) Assignee: Hypodest Patent Development Company - Patentes LDA, Madera (PT)

( * ) Notice: Subject to any disclaimer, the term of this patent is extended or adjusted under 35 U.S.C. 154(b) by 0 days.

(21) Appl. No.: 09/530,784

(22) PCT Filed: Nov. 4, 1998

(86) PCT No.: PCT/FR98/02357

§ 371 Date: May 5, 2000

§ 102(e) Date: May 5, 2000

(87) PCT Pub. No.: WO99/24096

PCT Pub. Date: May 20, 1999

(30) Foreign Application Priority Data

Nov. 6, 1997 (FR) .............................................. 97 13974

(51) Int. Cl.⁷ ........................ A61M 05/32; A61G 12/00
(52) U.S. Cl. ...................................................... 219/68
(58) Field of Search ........................................... 219/68

(56) References Cited

U.S. PATENT DOCUMENTS 5,245,935 A * 9/1993 Fukuda ......................... 219/68
5,468,928 A    11/1995 Yelvington ................... 219/68

FOREIGN PATENT DOCUMENTS

| FR | 2 745 187    |   | 8/1997  |
| GB | 2 260 707    |   | 4/1993  |
| GB | 2297230      | * | 7/1996  |
| JP | 2-52652      | * | 2/1990  |
| JP | 6-125945     | * | 5/1994  |
| WO | WO 93/00121  |   | 1/1993  |
| WO | WO 94/28852  |   | 12/1994 |
| WO | WO 96/38255  |   | 12/1996 |

* cited by examiner

Primary Examiner—Geoffrey S. Evans
(74) Attorney, Agent, or Firm—Young & Thompson

(57) ABSTRACT

A process and an apparatus for the individual destruction of syringe needles by melting under the effect of a high-intensity electric current. The apparatus includes a lower electrode adapted to accommodate the free end of a needle and to form therewith an electrical contact, connected electrically to a first terminal of an electric power source, a first upper electrode connected electrically to a second terminal of the electric power source. The apparatus also includes a second upper electrode adapted to be placed in electrical contact with the surface of the needle at least substantially radially opposite the first upper electrode. The second upper electrode is connected electrically to the first terminal.

23 Claims, 4 Drawing Sheets

Figure 1:
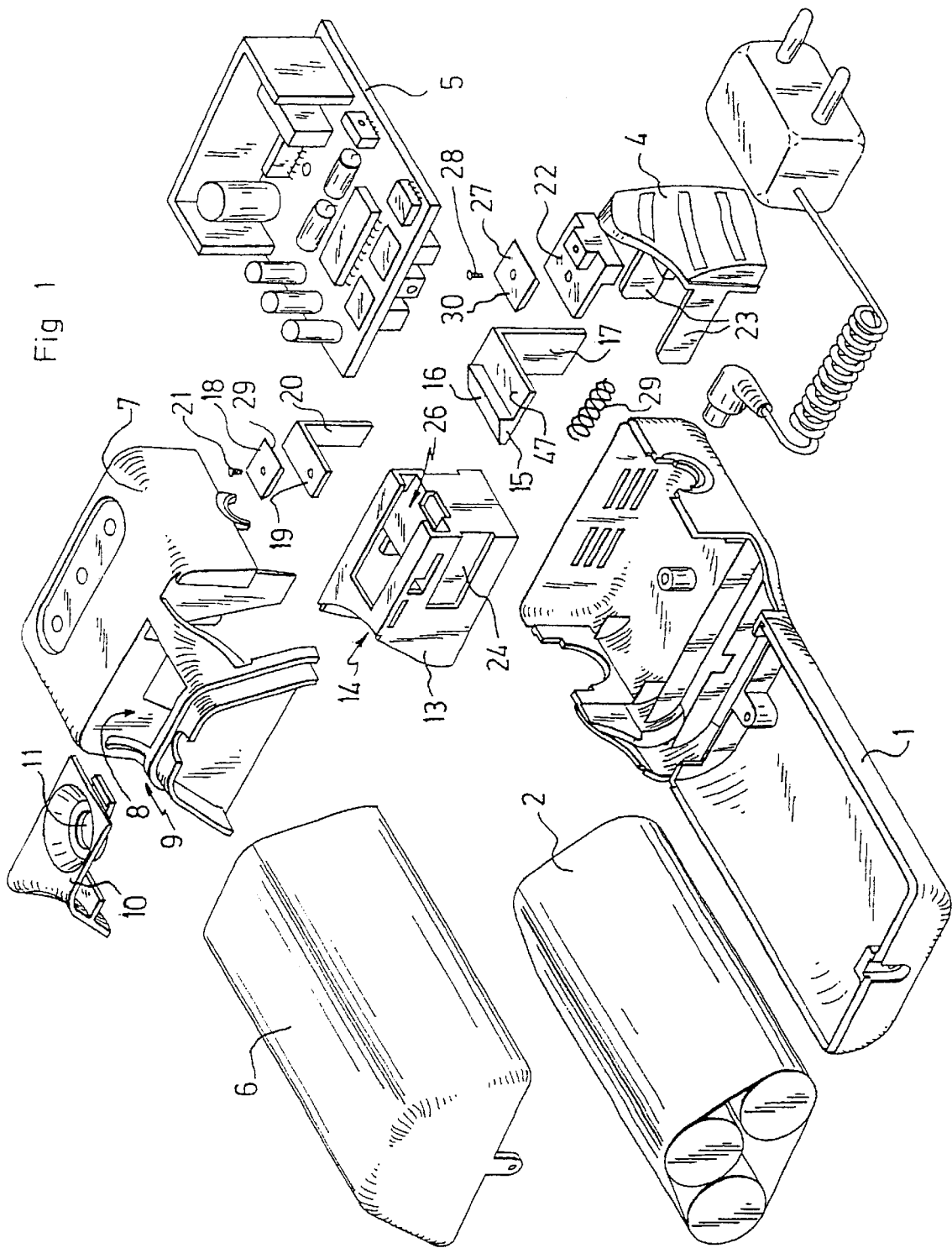

Fig 4
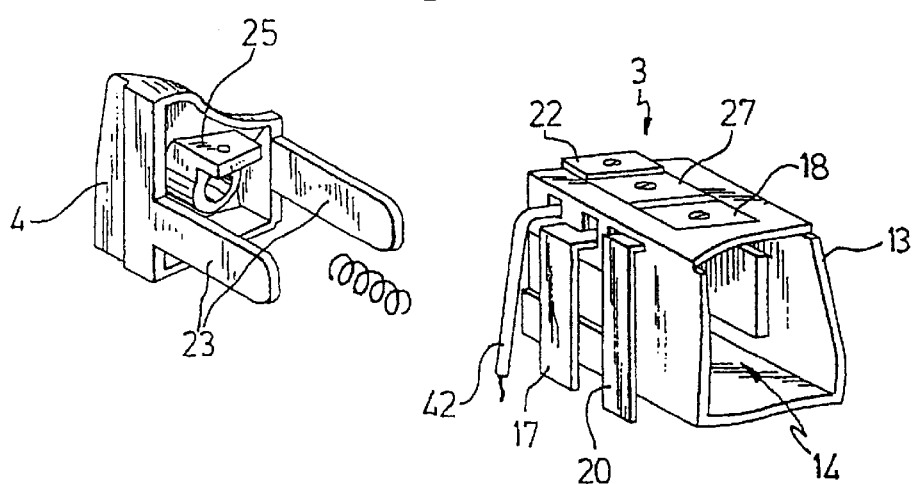
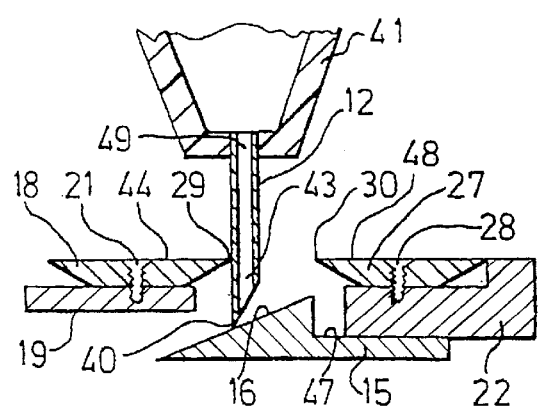
Fig 5a
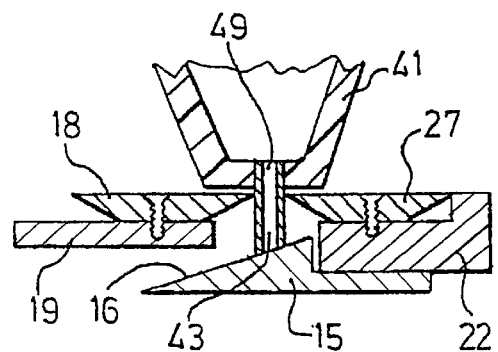
Fig 5b

METHOD AND APPARATUS FOR INDIVIDUAL DESTRUCTION OF SYRINGE NEEDLES BY MELTING UNDER THE EFFECT OF ELECTRIC CURRENT

The invention concerns a process and an apparatus for the individual destruction of syringe needles by melting under the effect of a high-intensity electric current.

Worn syringe needles are dangerous waste and they constitute in particular a carrier for the transmission of viruses.

Apparatuses have already been proposed enabling worn syringe needles to be destroyed by melting under the effect of an electric arc. For example, WO-A-9300121 describes an incinerating device for needles comprising a pair of fixed electrodes for the progressive melting of the needle and clamping means enabling the residue of the needle to be sealed off at the end of the melting process. This device comprises a piston having an opening through which the needle is introduced. This opening cannot be traversed by the end piece carrying the needle, which has a larger diameter and which butts up against the piston at the end of the stroke. The piston is moved towards the electrodes until a micro-switch is actuated which activates an electric motor bringing about the clamping and plastic deformation of the residue of the needle between a pair of clamping jaws moved by the motor. The pair of clamping jaws may also be connected to an electric power source so as to enable an electric current to be applied between them, after a needle has been clamped, in order to seal the inside of the residual end of the needle. This complex and motorized device requires a high-capacity source of electricity and is heavy and bulky. It is not portable and has a life span limited by that of the electrodes. Moreover, it should be noted that since the clamping jaws are interposed between the piston and the electrodes, a residual length of the needle is still of necessity left at the extremity of the end piece of the needle or the syringe. Now, the inventors have found that this residual portion of the needle is as dangerous as, if not more so than a complete needle. In point of fact, it has been proved in practice that the small dimensions of this residual portion of the needle, far from reducing the risks of injury as could be expected, are in practice the cause of many accidents due to the fact that it is virtually invisible and has a deceptively inoffensive appearance.

Other similar devices have been proposed. In all cases however, a residual portion of the needle persists projecting from the extremity of the syringe end piece. This end portion can of course be cut into sections mechanically with the aid of a specific tool. Nevertheless, the problem still remains that the detached residual portion is not destroyed and is on the contrary sharp and potentially contaminated.

In addition, most of the devices previously proposed for destroying needles with the aid of an electric current are either bulky and not portable (in particular supplied by the electric mains), or are portable but are insufficiently independent or are not sufficiently effective to melt all needles. Moreover, all these apparatuses are extremely costly and have a limited life span due to the rapid wear of the electrodes, so that their use on a large scale for equipping personnel of the health occupations (nurses, physicians, dentists, hospital personnel, pharmacists, ambulance staff, first aid staff, fire fighting personnel, veterinary surgeons, etc.) or patients (diabetic patients etc.) cannot reasonably be considered.

In all the text, the expression "syringe end piece" designates, in a syringe comprising a syringe body carrying a needle, the end piece which carries the hollow tapered metal stem, the so called needle stem, forming the actual needle. The concept of "a syringe end piece" also encompasses in a similar manner the case where the needle is connected to a flexible tube acting as the syringe body (dialysis or sampling line, etc). More generally, in all the text, the term "syringe" applies to any device for injecting liquids into, or sampling liquids from, a system to which a needle is associated, projecting from an end piece, the so-called syringe end piece. More often, the syringe end piece is formed of the female end piece of the needle carrying the needle stem, and which is connected to a mating male end piece of the syringe body. The syringe end piece has, at its end through which the needle stem emerges, a shoulder extending at least substantially radially outwards with respect to the needle stem and this end piece is slightly flared out towards the body of the syringe, the assembly between the male and female end pieces being generally of a conical type. This shoulder has a larger diameter than the needle stem.

The object of the invention is thus to overcome the above mentioned disadvantages by providing a process and an apparatus for the purpose of destruction by virtue of which each needle may be entirely destroyed without any dangerous waste or sharp residual portion projecting from the syringe end piece.

More particularly, the object of the invention is to provide a portable apparatus enabling needles to be entirely destroyed over all their axial length projecting from the syringe end pieces.

The object of the invention is more particularly to provide an apparatus which can be used with all needles, whatever their dimensions, in particular up to a diameter of the order of 1.2 mm.

The object of the invention is also to provide an apparatus having a considerable degree of autonomy which enables a large number of needles to be destroyed, in particular more than 80 needles with a diameter of 0.6 mm, between two recharges or two renewals of the electric power source.

The object of the invention is moreover to provide such an apparatus which is particularly simple and reliable, has a long life, is safe to use, and of which the cost is much lower, in particular three to five times lower, than that of previously known devices.

The object of the invention is moreover to provide a portable apparatus which is particularly ergonomic, easy and inexpensive to use and maintain, and which is light and small.

In all the text, the term "axial" and its derived terms designate a direction parallel to the axis of a needle to be destroyed, and the term "radial" and its derived terms designate a direction perpendicular to the axial direction. Moreover, the apparatus is assumed to be horizontal overall and the needle vertical overall with its free end downwards, although in practice this position is of course not compulsory. In addition, the expressions "end portion of the needle" and "residual end portion of the needle" designate end portions of the tapered metal hollow stem forming the needle itself and therefore does not encompass the syringe end piece.

The invention thus concerns a process for the individual destruction of syringe needles by melting under the effect of a high-intensity electric current with the aid of electrodes connected via a power circuit to an electric power source, in which, in a first destruction step, the free end of a needle is applied in electrical contact with a lower electrode connected electrically to a first terminal of the electric power source, the outer surface of the needle is applied in electrical contact with a first upper electrode connected electrically to a second terminal of the electric power source which is distinct from the first terminal to which the lower electrode is connected, the distance between the electrical contact of the outer surface of the needle with the first upper electrode and the free end of the needle in electrical contact with the lower electrode being adapted so that the electric current established between the lower electrode and the first upper electrode via an end portion of the needle extending between these electrodes is capable of bringing about the melting of this end portion of the needle, and the needle is progressively melted by causing its outer surface in contact with the first upper electrode to slide axially as melting of the end portion progresses, wherein:

the first upper electrode has a free upper face against which a syringe end piece can butt up axially, in a first destruction step, the needle is progressively melted by causing its outer surface in contact with the first upper electrode to slide axially until the syringe end piece carrying the needle arrives so as to butt up axially against the first upper electrode, in a second subsequent destruction step, the second upper electrode is applied in electrical contact with the outer surface of the needle at least substantially radially opposite the first upper electrode, this second upper electrode being connected electrically to the same first terminal of the electric power source which is distinct from the second terminal to which the first upper electrode is connected, so that an electric current is established between the first upper electrode and the second upper electrode through the cross section of the needle flush with the syringe end piece butted up against the first upper electrode, whereby the residual end portion of the needle extending in projection from the syringe end piece is destroyed by electrical melting, flush with the end piece of this syringe, this residual end portion being destroyed by melting between the first upper electrode and the second upper electrode, and the melt residue being moreover detached from the syringe end piece which subsequently no longer presents any projecting asperities.

Advantageously and according to the invention, during the second destruction step, the first upper electrode and the second upper electrode are applied against the outer surface of the needle while exerting a radial pressure against them by manual action tending to bring them together while pinching the section of the needle.

Advantageously and according to the invention, the second upper electrode is applied with a radial pressure against the outer surface of the needle, whereas the outer surface of the needle is, on the other hand, butted up radially against the first upper electrode carried by a framework of the apparatus.

Thus, according to the process of the invention, during the subsequent second destruction step, the residual end portion of the needle stem, flush with the syringe end piece, is destroyed by electrical melting between the two upper electrodes. The melt residue is moreover detached from the syringe end piece which subsequently no longer presents sharp projecting asperities. On the contrary, the heat produced by melting the end portion by means of the two upper electrodes, tends to melt the extremity of the syringe end piece, at least partially, which has the effect of blocking it and presenting a particularly harmless surface appearance.

Since the residual end portion is destroyed by electrical melting, no complex motorized mechanical device for mechanical sectioning has to be provided, it being possible for the contact of the upper electrodes with this residual portion of the needle to be obtained by manual action. Nothing however will prevent means being provided which will make it possible to assist or facilitate this manual action, for example a spring providing a return action in the direction of separation, or on the other hand, of approach of the upper electrodes.

It should moreover be noted that the progressive melting of the needle at a high temperature (practically at a temperature greater than 1300° C.) has the effect of bringing all the metal needle to a high temperature, including the portion of the needle which extends inside the syringe end piece. Destruction of micro-organisms and viruses is therefore obtained and hence sterilization of the syringe end piece.

The invention also extends to an apparatus for implementing the process according to the invention.

The invention also concerns an apparatus for the individual destruction of syringe needles by melting under the effect of a high-intensity electric current, comprising an electric power source and electrodes connected to the electric power source via a power circuit, these electrodes being adapted so that they can be placed in contact with a needle so as to establish between them, via a portion of the needle extending between these electrodes, an electric current which can bring about melting of this portion of the needle, these electrodes comprising:

a lower electrode adapted so as to receive the free end of a needle and to form therewith an electrical contact, this lower electrode being connected electrically to a first terminal of the electric power source, a first upper electrode adapted so that it can be placed in electrical contact with the outer surface of the needle at an axial distance from the free end of the needle in contact with the lower electrode adapted so that the electric current established between the lower electrode and the first upper electrode via an end portion of the needle extending between these electrodes, is able to bring about melting of this end portion of the needle, this first upper electrode being connected electrically to a second terminal of the electric power source which is distinct from the first terminal to which the lower electrode is connected, wherein:

the first upper electrode has a free upper face against which a syringe end piece can butt up axially, the electrodes include a second upper electrode adapted so that it can be placed in electrical contact with the outer surface of the needle at least substantially radially opposite the first upper electrode, this second upper electrode being connected electrically to the same first terminal of the electric power source which is distinct from the second terminal to which the first upper electrode is connected, so that an electric current can be established between the first upper electrode and the second upper electrode, through the section of the needle, whereby a residual end portion of the needle extending as a projection from the syringe end piece carrying the needle after the needle has been progressively melted between the first upper electrode and the lower electrode, can be destroyed by electrical melting between the first upper electrode and the second upper electrode, flush with the syringe end piece butted up against the first upper electrode, this residual end portion of the needle, the melt residue, being moreover detached from the syringe end piece which subsequently no longer presents any projecting asperities.

Advantageously and according to the invention, the free upper face of the first upper electrode against which the syringe end piece can butt up axially, presents a sharp straight edge against which the outer surface of the needle can be applied radially in order to establish tangential contact with this sharp straight edge.

Similarly, advantageously and according to the invention, the second upper electrode has a free upper face against which a syringe end piece can butt up axially, and a sharp straight edge which is defined by this free upper face and which may be applied radially against the outer surface of the needle in order to establish tangential contact with this sharp straight edge.

Advantageously and according to the invention, the first upper electrode and/or the second upper electrode is formed of an insert mounted in a detachable manner on a conducting electrode support.

Advantageously and according to the invention, the insert has several, in particular four, sharp straight edges and is mounted on the electrode support so as to make it possible to change the sharp straight edge designed to come into electrical contact with the outer surface of a needle. Advantageously, the insert has a square free upper face.

In addition, advantageously and according to the invention, the first upper electrode and/or the second upper electrode are/is made of tungsten carbide.

In addition, advantageously and according to the invention, the apparatus is characterized in that the first upper electrode is mounted fixed with respect to a frame of the apparatus and in that the second upper electrode is mounted so that it can be displaced radially in translation between a position away from the first upper electrode where only this first upper electrode is in contact with the outer surface of a needle and a position close to the first upper electrode where these two electrodes are in electrical contact with the outer surface of a needle.

Advantageously and according to the invention, the second upper electrode is mounted secured in translation to a push button adapted so that it can be actuated manually.

In addition, the invention also concerns an apparatus for the individual destruction of syringe needles by melting under the effect of a high-intensity electric current, comprising an electric power source and electrodes connected to the electric power source via a power circuit, these electrodes comprising a lower electrode adapted so as to receive the free end of a needle and to form therewith an electrical contact, this lower electrode being connected electrically to a terminal of the electric power source, and a first upper electrode adapted so that it can be placed in electrical contact with the outer surface of the needle, this first upper electrode being connected electrically to a terminal of the electric power source which is distinct from the terminal to which the lower electrode is connected, wherein:

the axial distance between the lower electrode and the electrical contact established between the outer surface of the needle and the first upper electrode is comprised between 3 mm and 5 mm, in particular of the order of 4 mm, the electric power source comprises a voltage source delivering, between two terminals, a continuous voltage comprised between 1.8 V and 2.5 V, the power circuit has a total internal resistance between the lower electrode and the first upper electrode via the electric power source, which is less than 50 mΩ so that the apparatus may in particular be portable.

It has indeed been found that with these values it is possible to bring the portion of the needle comprised between the lower electrode and the first upper electrode to a high temperature (above 1300° C.) and to melt this portion of the needle, and this with the most common commercial shapes and dimensions of needles. In particular, it is found that in spite of the low continuous voltage used (less than 2.5 V), an intensity greater than 60 A is achieved between the two electrodes.

Advantageously and according to the invention, the electric power source comprises at least one pair of cells or accumulators in series, each cell or accumulator delivering a voltage of the order of 1.2 V.

Advantageously and according to the invention, the electric power source comprises several, in particular three, pairs of cells or accumulators mounted in parallel, each cell or accumulator having a capacity above 1500 mAh, in particular of the order of 1800 mAh.

Preferably and according to the invention, the electric power source is formed of rechargeable cadmium-nickel accumulators.

In addition, it is important that the internal resistance of the power circuit is below 50 mΩ, and is as low as possible, in order to prevent any resistive losses and voltage drops before the electrodes are supplied. Advantageously and according to the invention, the apparatus is in addition characterized in that the power circuit includes at least one controlled electronic switching circuit which makes it possible to supply or isolate at least one of the electrodes from the corresponding terminal of the electric power source, and in that this controlled electronic switching circuit is adapted so as to have an internal resistance, in the closed state when the electrode is supplied, which is less than 15 mΩ, in particular of the order of 10 mΩ.

Advantageously and according to the invention, the controlled electrical switching circuit includes an MOS transistor, and the apparatus includes a voltage booster circuit enabling the transistor to be polarized from the electric power source. The voltage booster circuit enables the MOS transistor to be polarized at a voltage greater than the voltage delivered by the electric power source. As a voltage booster, it is possible to use for example, a voltage multiplier assembly, in particular of the Latour or Schenkel type consisting of diodes and capacitors.

In addition, the apparatus according to the invention advantageously includes a secondary electronic circuit making it possible in particular to control the operation of the apparatus (with a start and stop button, indicator lights, a charging circuit enabling the accumulators to be recharged from a transformer connected to the mains, a timer circuit making it possible to limit the duration of polarization of the electrodes while waiting for a needle to be destroyed, and a circuit controlling the electronic switching circuit (control and polarization of the switching of the MOS transistor applied to its grid etc)). Advantageously and according to the invention, this secondary electronic circuit includes an electrical supply circuit with capacitor(s) connected to the electric power source, and adapted so as to supply the electronic components of the apparatus while the needle is being melted. In this way, while an electric current is established between the electrodes and the needle is being melted, all the intensity delivered by the electric power source can be provided to the electrodes, the secondary electronic circuit being supplied from the electrical energy previously stored in the electrical supply circuit with capacitor(s).

In practice, it is found that the apparatus according to the invention is extremely simple, efficient and is not bulky (its typical dimensions being 170 mm×70 mm×43 mm); is light (less than 550 g); has considerable electrical autonomy enabling more than 80 needles of a diameter of 0.6 mm to be destroyed between recharges; may be constructed at low cost; has a long life; is particularly ergonomic, simple to use and maintain; and it enables each of the needles to be entirely destroyed after use without leaving any residual portion projecting from the syringe end piece or any dangerous sharp, contaminated residue. It is thus possible to consider equipping all the personnel of the health services and/or patients with an apparatus according to the invention.

The invention also concerns a process and an apparatus characterized in combination by all or part of the characteristics mentioned above or hereinafter.

Figure 2:
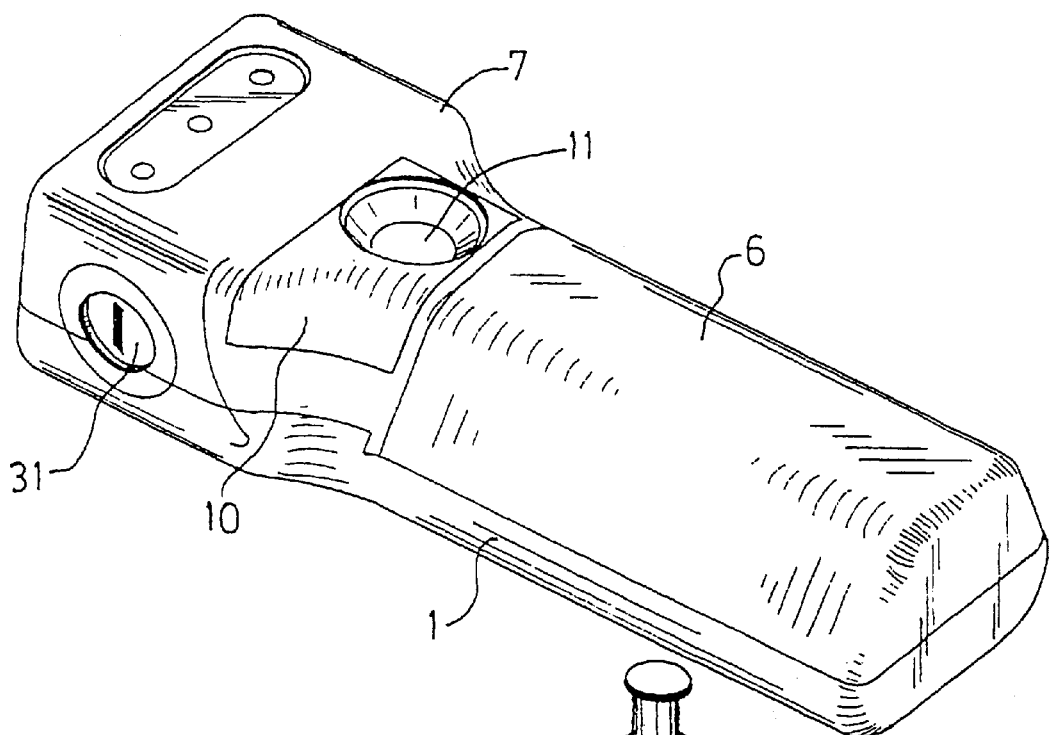
Figure 3:
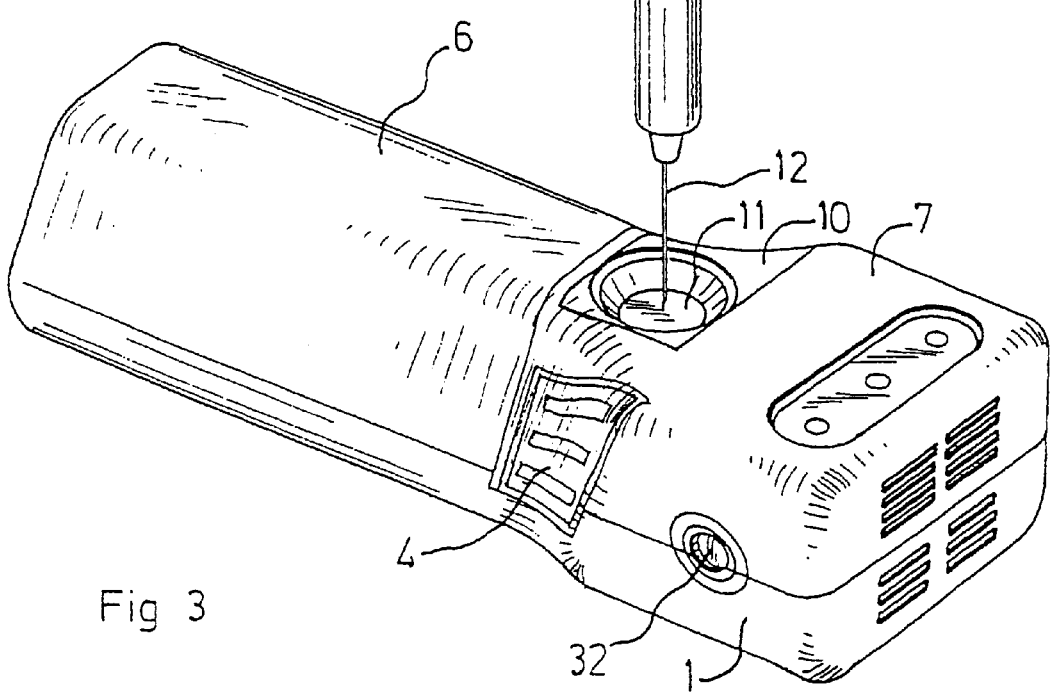
Figure 6:
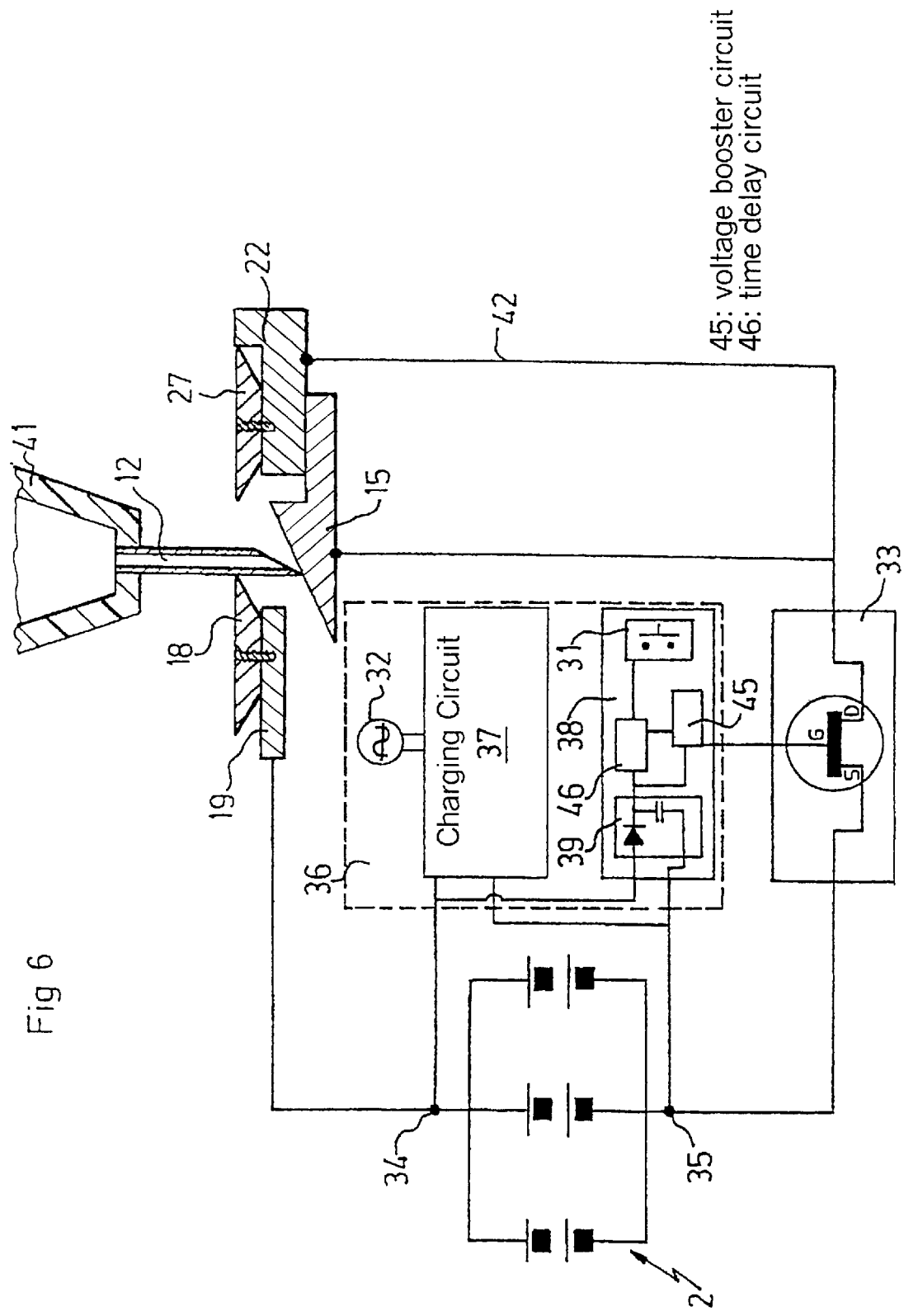

Other objects, characteristics and advantages of the invention will become apparent on reading the following description which refers to the accompanying figures in which:

FIG. 1 is an exploded perspective diagrammatic view of an apparatus according to one preferred embodiment of the invention, FIGS. 2 and 3 are external perspective diagrammatic views of an apparatus according to one preferred embodiment of the invention, along two different angles of view respectively, FIG. 4 is an exploded perspective detailed diagrammatic view of an electrode-carrier cassette and a push button of an apparatus according to the invention, FIGS. 5a and 5b are vertical sectional diagrammatic views illustrating respectively two steps of a process according to the invention, FIG. 6 is an electronic circuit diagram of an apparatus according to one embodiment of the invention, Apparatus 1 according to the invention shown in the figures comprises the bottom of a box 1 forming a frame receiving a battery of accumulators 2, an electrode-carrier cassette 3 associated with a push button 4, and an electronic board 5.

The box is closed at the upper part by two upper covers 6, 7, one of which 6 covers the battery of accumulators 2, while the other, 7, covers the electrode-carrier cassette 3 and the electronic board 5. This latter cap 7 is provided with an opening 8 giving access to the electrode-carrier cassette 3 and to the electrodes from above, and a side opening 9 making it possible to empty the cassette 3 of the residues of melted needles through the side. The openings 8 and 9 may be formed of one and the same opening or of two distinct openings. The openings 8 and 9 are covered by a carrier bracket 10 mounted in a detachable manner on the cover 7. This carrier bracket 10 is provided with a circular opening 11 for the passage of a needle 12 to be destroyed. This opening 11 has a shape and transverse dimensions greater than those of the syringe end piece, so that the latter can pass through the opening 11.

The electrode-carrier cassette 3 includes a part made of insulating material 13 in the general shape of a tunnel, provided with openings and recesses to receive different electrodes. This tunnel-shaped part 13 serves to receive the residues of the melted needles, and has a side opening 14 disposed opposite the side opening 9 of the box so that these residues can be emptied.

The apparatus includes a lower electrode 15 mounted in a fixed manner in the electrode-carrier cassette 3 and having a flat 16 sloping at an angle of the order of 450 to the horizontal, which extends immediately under the opening 11 of the carrier bracket 10 when the latter is put in place. This lower electrode 15 extends at least over part of the width of the tool carrier cassette 3 and has a lug 17 extending the lower electrode 15 outside the part 13 laterally and downwards. The lower end of the face 17 of the lower electrode 15 is connected electrically to the electronic board 5, for example by a soldered joint.

The electrode-carrier cassette 3 also includes a first electrode support 19 extending over the width of the tunnel-shaped part 13 at a distance from the lower electrode 15 and parallel to the lower edge of its sloping flat 16. This first electrode support 19 is extended outside the tunnel-shaped part 13 laterally and downwards by a lug 20 of which the lower free end is connected electrically to the electronic board 5 for example by a soldered joint. This first support 19 is mounted in a fixed manner with respect to the tunnel-shaped part 13 and therefore on the tool-carrier cassette 3, which is itself mounted in a fixed manner on the bottom of the box 1 forming the frame. Similarly the lower electrode 15 is mounted in a fixed manner with respect to the part 13 and is therefore fixed with respect to the electrode-carrier cassette 3 and the bottom of the box 1 forming the frame.

The first electrode support 19 receives a first upper electrode 18 which is formed of an insert made of tungsten carbide (sintered metal) fixed by a screw 21 onto the first support 19.

The second electrode support 22 is mounted securely to the push button 4 which is itself mounted and guided in translation with respect to the tunnel-shaped part 13 by means of two horizontal lugs 23 of the push button 4 sliding in lateral grooves 24 of the part 13. The second electrode support 22 is mounted on a bracket 25 of the push button 4 by means of a pin and is adapted so that it can be introduced and slid in translation in a rail 26 formed by the tunnel-shaped part 13 and on one upper horizontal face 47 of the lower electrode 15. The second electrode support 22 accommodates a second upper electrode 27 which is formed of an insert made of tungsten carbide (sintered metal) fixed on the second electrode support 22 by means of a screw 28.

The lower electrode 15, the first electrode support 19 and the second electrode support 22 are formed of copper or brass parts. The push button 4 is formed of a part made of synthetic material. A spring is interposed between the push button 4 and the vertical face opposite the tunnel-shaped part 13 so as to return the push button 4 to a position separated laterally from the electrode-carrier cassette 3.

Each of the upper electrodes 18, 27 is formed of an insert in the general shape of a truncated pyramid of which the small base comes into contact with the corresponding electrode support 19, 22. The large base 44, 48 of each of these inserts forms a free upper polygonal face 44, 48 (in particular square) defining several sharp straight edges 29, 30 respectively (in particular four sharp straight edges) 29,30 respectively at 30–90° to each other. The inserts forming the first upper electrode 18 and the second upper electrode 27 can thus be dismantled from their respective electrode supports 19, 22. When the sharp edge 29, 30 of the insert coming into contact with the outer surface of the needles to be destroyed is worn or is damaged, it is sufficient to unscrew the screw 21, 28 and to turn the insert through 90° in order to present a fresh sharp edge in the new state. Moreover, when all the edges are worn, it is easy to change the inserts for new ones.

The opening 11 of the carrier bracket 10 is adapted so as to serve as a reference for the start of the introduction of the needle. Nevertheless, it should be noted that once the needle is engaged in the electrodes 15, 18, the opening 11 no longer acts as a guide, the needle being guided solely by the electrodes 15, 18 and not coming into contact with the opening 11.

The two upper electrodes 18, 27 are mounted so as to be radially opposite each other. In other words, the sharp edges 29,30 of the two upper electrodes 18, 27 and their points of contact with the outer surface of the needle are situated in the same plane which is at least substantially radial to the needle.

The apparatus additionally includes a point 32 for connection to an outer electrical supply (mains or transformer or an accumulator charging circuit) as well as a side starting button 31.

As will be seen in the diagram of FIG. 6, the first upper electrode 18 is electrically connected, by the first electrode support 19, to the positive terminal 34 of the battery of accumulators 2. The lower electrode 15 and the second upper electrode 27 are connected, via a controlled electronic switching circuit 33, to the negative terminal 35 of the battery of accumulators 2. The function of the switching circuit 33 is to connect the electrodes 15,27 electrically to the negative terminal 35 of the battery of accumulators 2 when the operator presses the start button 31. The function of the switching circuit 33 is also to isolate the electrodes 15, 27 from the negative terminal 35 of the battery of accumulators 2 when the apparatus is not operating.

The battery of accumulators 2 consists of three pairs of accumulators 2, two accumulators of the same pair being mounted in series, the different pairs of accumulators 2 being mounted in parallel between the positive 34 and negative 35 terminals of the battery thus constituted. Each accumulator delivers a voltage of the order of 1.2 V, so that a continuous voltage of the order of 2.4 V is delivered between the terminals 34, 35 of the battery 2. Each accumulator has a capacity greater than 1500 mAh, in particular of the order of 1800 mAh. The accumulators are preferably and according to the invention, rechargeable cadmium-nickel accumulators. They are moreover chosen to have a low internal resistance.

It should be noted that care must be taken that the internal resistance of the accumulators themselves, the resistance of the connecting wires, and the internal resistance of the switching circuit 33 are such that the entire power circuit can have a value below 50 mΩ. Moreover, by placing the pairs of accumulators 2 in parallel, the current delivered by each accumulator is divided accordingly. In this way, it is possible to increase the period during which the current may be delivered. Simultaneously, the assembly of the accumulators makes it possible to reduce the internal resistance of the battery of accumulators 2.

The controlled electronic switching circuit 33 includes, advantageously and according to the invention, an MOS transistor with a switching field effect polarized by a voltage booster circuit 45 (voltage multiplier of the Latour or Schenkel type) making it possible to polarize it from the battery of accumulators 2.

The output from the voltage booster circuit 45 is connected to the grid of the MOS transistor. The source of the transistor is connected to the negative terminal 35 of the battery 2, whereas its drain is connected to the electrodes 15, 27 which must be connected to or isolated from this terminal 35.

A secondary electronic circuit 36 makes it possible to control the operation of the apparatus. This circuit 36 is connected to the positive and negative terminals of the battery of accumulators 2 and includes an electrical supply circuit 39 having a capacitor(s) which makes it possible to accumulate the electrical energy necessary for operating the different electronic components of the apparatus while the electrodes 15, 18, 27 are supplied during the melting of the needle 12. This circuit 39 includes for example a capacitor connected between the terminals 34,35 via a diode.

In the embodiment shown in FIG. 6, the secondary electronic circuit 36 includes a circuit 37 for charging the battery of accumulators 2, this circuit 37 being connected to the mains connector 32. This charging circuit 37 is for example formed of a rectifier and a circuit forming a source of current. The secondary electronic circuit 36 also includes a logic control circuit 38 for the switching circuit 33, capable of delivering a control signal when the operator presses the start button 31. Moreover, the circuit 38 includes the circuit 39 with capacitor(s) which provides the electrical supply for this circuit 38 and the different circuits managing the operation of the apparatus.

The power circuit formed by the battery of accumulators 2, and between the positive terminal 34 of the battery of accumulators 2 and the first upper electrode 18 on the one hand, and between the negative terminal 35 and the lower electrode 15 via the switching circuit 33 on the other hand, is adapted so as to have a total internal resistance which is as low as possible and which is less than 50 mΩ.

FIGS. 5a, 5b and 6 show the general arrangement of the electrodes as the needle 12 is being destroyed. As can be seen, during the first destruction step, the start button 31 is actuated and the free end 40 of the needle 12 is applied in contact with the lower electrode 15, more exactly in contact with the inclined flat 16 of this lower electrode 15. The outer surface of the needle 12 is then applied in contact with the sharp edge 29 of the first upper electrode 18. Since the apparatus is in operation, an electric current is established, which brings about the melting of the end portion 43 of the needle extending between the edge 29 of the first upper electrode 18 and the inclined flat 16 of the lower electrode 15. As the destruction and melting of the needle progresses, the operator gently pushes the syringe downwards. It should be noted that the slope of the inclined flat 16 of the lower electrode 15 directed towards the first upper electrode 18 tends to hold the outer surface of the needle 12 in contact with the sharp edge 29 of the first upper electrode 18. The high intensity of the electric current circulating through this end portion 43 of the needle has the consequence of raising it to a very high temperature (in particular to a temperature above 1300° C.) and hence of melting this portion of the needle. Moreover, this very high temperature is propagated inside the needle 12 up to the end piece 41 which carries the needle 12, or even inside the actual interior of the body of the syringe. In practice, it has been possible to determine by measurement that the temperature inside the portion of the needle extending inside the end piece 41 manages to exceed 350° C. and enables this portion 49 of the needle and the end piece 41 to be sterilized. The melt residues from the end portion 43 of the needle fall along the inclined flat 16 inside the electrode-carrier cassette 3 and are collected inside the tunnel-shaped part 13.

The needle 12 is destroyed in this way until the end piece 41 butts up against the free upper face 44 of the first upper electrode 18 and possibly against the free upper face 48 of the second electrode 27, according to the distance presented between the upper electrodes 18, 27. In order to terminate the destruction of the needle, the operator then actuates the push button 4 manually with a view to bringing the second upper electrode 27 towards the needle 12, as shown in FIG. 5b. It should be noted that this second upper electrode 27 is connected to the negative terminal 35 of the battery of accumulators 2, the switching circuit 33 being closed. To this end, a conductor 42 is preferably provided directly connected electrically to the second electrode support 22, although this second electrode support 22 rests in fact on the flat conducting face 47 of the lower electrode 15. In point of fact, it is in this way ensured that the electrical supply to the second upper electrode 27 is of good quality (low resistance).

Similarly, the electrical connecting lugs 17, 20 of the first electrode support 19 and the lower electrode 15 respectively, together with the electronic board 5, are directly soldered and connected electrically to the electronic circuit formed by the electronic board 5. Accordingly, and by virtue of the simultaneous use of an MOS transistor with a low internal resistance, a power circuit is achieved with a low internal resistance so that the potential difference between the electrodes corresponds at least substantially to the voltage delivered by the battery of accumulators 2 between these terminals 34, 35.

In the position shown in FIG. 5b, it should be noted that the free end 43 of the residual portion of the needle 12 is no longer in contact with the lower electrode 15 since, in general, some degree of melting of the end portion 43 has previously occurred. In the embodiment shown, advantageously and according to the invention, the two upper electrodes 18, 27 are diametrically opposite with respect to the outer cylindrical surface of the needle 12, and their sharp edges 29, 30 in electrical contact with this outer surface are at least substantially parallel. By bringing the second upper electrode 27 closer in contact with the outer surface of the needle 12, and opposite the first upper electrode 18, the electric current is established radially through the thickness of the needle 12, which has the effect of causing it to melt. The residual portion of the needle 12 is destroyed by melting flush with the end piece 41 without any projecting part being left. In addition, the heat given off between the electrodes 18, 27 has the effect of melting, at least partially, the end portion 43 and the portion 49 of the needle embedded in the end piece 41, and the synthetic material constituting the end piece 41, which blocks the emerging orifice emerging of the residual portion 49 of the needle inside the end piece 41. When the user releases the push button 4, this is returned laterally outwards so that the second upper electrode 27 moves away laterally and radially from the first upper electrode 18.

The secondary electronic circuit 36 advantageously includes indicator lights for indicating in particular that the apparatus is operational after actuating the start button 31, or that the battery of accumulators 2 is being charged, or it includes an alarm indicating an excess temperature in the electrical power circuit (MOS transistor). The secondary electronic circuit 36 also advantageously includes a time delay circuit 46 having a delay for closing the switching circuit 33 whilst allowing the needle 12 to be destroyed only for a predetermined period, for example of the order of 15 seconds, after which the switching circuit 33 is automatically put back into the open state.

Moreover, the logic control circuit 38 of the switching circuit 33 includes means for controlling the temperature, adapted so as to interrupt the electrical supply to the electrodes, i.e. to order the switching circuit 33 to be in the open state (by applying a signal blocking the MOS transistor on its grid), when the temperature of the accumulators 2 exceeds a predetermined value. These means for controlling the temperature are adapted so as to allow electricity to be supplied once again to the electrodes, i.e. the closure of the switching circuit 33 (or the application of a signal to the grid of the MOS transistor placing it in the conducting mode) when the temperature of the accumulators falls once again below this predetermined value (i.e. to a normal value). These means for temperature control advantageously include an element sensing the operational temperature of the MOS transistor itself. In point of fact, the heating of the MOS transistor and of the accumulators are associated phenomena. It should be noted that this thermal protection assists in extending the life of the battery of accumulators 2 since, on the one hand it prevents the accumulators 2 from overheating and, in addition, it ensures a period of rest after the start of each overheating.

The invention thus makes it possible to achieve the total destruction of needles in an extremely simple and efficient manner. In particular, the destruction of the needle flush with the end piece 41 encourages sterilization and blocks the protruding orifice of the residual metal portion 49 of the needle passing through the end piece 41. This destruction is due to the melting of the needle by the Joule effect. The portion 49 of the needle remaining incrusted in the syringe end piece 41 is blunted, is no longer sharp or pointed and does not project outwards so that it is totally harmless. The pressure exerted by the user on the push button 4 can assist in the destruction but it is not in fact necessary as soon as electrical contact is established between the upper electrodes 18, 27. In practice, it is possible to obtain sufficient electrical contact for the destruction with the aid of the force from one finger exerting a pressure on the push button 4. The upper electrodes 18, 27 provided with sharp bevelled edges 29, 30 also facilitate the destruction of the needle by melting by creating a zone for the concentration of the electric current. The fact that they are made of tungsten carbide is also favourable, in particular for questions of long life.

The invention is the object of many variants in relation to the embodiment described above and shown in the figures. In particular, it is possible to provide a supplementary switching circuit for controlling the supply to the second upper electrode 27.

It should be noted that the selected choice of dimensions, and in particular the distance between the lower electrode 15 and the first upper electrode 18, comprised between 3 and 5 mm, in particular of the order of 4 mm; the assembly of six accumulators and the choice of a voltage delivered of between 1.8 and 2.5 V in particular of the order of 2.4 V; and the construction of the power circuit with a low internal resistance, make it possible to optimize the dissipation of electrical energy by the Joule effect within the needle and finally to obtain a good overall yield for the melting process from a small number of small size accumulators.

What is claimed is:

1. A process for the individual destruction of syringe needles by melting under the effect of a high-intensity electric current with the aid of electrodes connected via a power circuit to an electric power source (2), in which, in a first destruction step, the free end (40) of a needle (12) is applied in electrical contact with a lower electrode (15) connected electrically to a first terminal (35) of the electric power source (2), the outer surface of the needle (12) is applied in electrical contact with a first upper electrode (18) connected electrically to a second terminal (34) of the electric power source (2) which is distinct from the first terminal (35) to which the lower electrode (15) is connected, the distance between the electrical contact of the outer surface of the needle (12) with the first upper electrode (18) and the free end (40) of the needle (12) in electrical contact with the lower electrode (15) being adapted so that the electric current established between the lower electrode (15) and the first upper electrode (18) via an end portion (43) of the needle extending between these electrodes (15, 18) is capable of bringing about the melting of this end portion (43) of the needle, and the needle (12) is progressively melted by causing its outer surface in contact with the first upper electrode (18) to slide axially as melting of the end portion (43) progresses, wherein:

a first upper electrode (18) is used which has a free upper face (44) against which a syringe end piece (41) can butt up axially, in a first destruction step, the needle (12) is progressively melted by causing its outer surface in contact with the first upper electrode (18) to slide axially until a syringe end piece (41) carrying the needle (12) arrives so as to butt up axially against the first upper electrode (18), in a second subsequent destruction step, the second upper electrode (27) is applied in electrical contact with the outer surface of the needle (12) at least substantially radially opposite the first upper electrode (18), this second upper electrode (27) being connected electrically to the same first terminal (35) of the electric power source which is distinct from the second terminal (34) to which the first upper electrode (18) is connected, so that an electric current is established between the first upper electrode (18) and the second upper electrode (27) through the section of the needle (12) flush with the syringe end piece (41) butted up against the first upper electrode (18), whereby the residual end portion (43) of the needle (12) extending in projection from the syringe end piece (41) is destroyed by electrical melting, flush with the end piece (41) of this syringe, this residual end portion (43) being destroyed by melting between the first upper electrode (18) and the second upper electrode (27), the melt residue being moreover detached from the syringe end piece (41) which subsequently no longer presents any sharp projecting asperities.

2. A process as claimed in claim 1, wherein a second upper electrode (27) is used which has a free upper face (48) against which a syringe end piece (41) can butt up axially.

3. A process as claimed in claim 1, wherein, during the second destruction step, the first upper electrode (18) and the second upper electrode (27) are applied against the outer surface of the needle (12) while exerting a radial pressure against them by manual action tending to bring them together while pinching the section of the needle (12).

4. A process as claimed in claim 1, wherein the second upper electrode (27) is applied with a radial pressure against the outer surface of the needle (12), whereas the outer surface of the needle (12) is, on the other hand, butted up radially against the first upper electrode (18) carried by a framework (1) of the apparatus.

5. An apparatus for the individual destruction of syringe needles by melting under the effect of a high-intensity electric current, comprising an electric power source (2) and electrodes connected to the electric power source (2) via a power circuit, these electrodes being adapted so that they can be placed in contact with a needle (12) so as to establish between them, via a portion of the needle extending between these electrodes, an electric current which can bring about melting of this portion of the needle, these electrodes comprising:

a lower electrode (15) adapted so as to receive the free end (40) of a needle (12) and to form therewith an electrical contact, this lower electrode (15) being connected electrically to a first terminal (35) of the electric power source (2), a first upper electrode (18) adapted so that it can be placed in electrical contact with the outer surface of the needle (12) at an axial distance from the free end (40) of the needle (12) in contact with the lower electrode (15) adapted so that the electric current established between the lower electrode (15) and the first upper electrode (18) via an end portion (43) of the needle extending between these electrodes (15, 18), is able to bring about melting of this end portion (43) of the needle, this first upper electrode (18) being connected electrically to a second terminal (34) of the electric power source (2) which is distinct from the first terminal (35) to which the lower electrode (15) is connected, wherein:

the first upper electrode (18) has a free upper face (44) against which a syringe end piece (41) can butt up axially, the electrodes include a second upper electrode (27) adapted so that it can be placed in electrical contact with the outer surface of the needle (12) at least substantially radially opposite the first upper electrode (18), this second upper electrode (27) being connected electrically to the same first terminal (35) of the electric power source (2) which is distinct from the second terminal (34) to which the first upper electrode (18) is connected, so that an electric current can be established between the first upper electrode (18) and the second upper electrode (27), through the section of the needle, whereby a residual end portion (43) of the needle extending as a projection from a syringe end piece (41) carrying the needle (12) after the needle (12) has been progressively melted between the first upper electrode (18) and the lower electrode (15), can be destroyed by electrical melting between the first upper electrode (18) and the second upper electrode (27), flush with the syringe end piece (41) butted up against the first upper electrode (18), the melt residue of this residual end portion of the needle being moreover detached from the syringe end piece (41) which subsequently no longer presents any projecting asperities.

6. An apparatus as claimed in claim 5, wherein the free upper face (44) of the first upper electrode (18) has a sharp straight edge (29) against which the outer surface of the needle (12) can be applied radially so as to establish tangential contact with this sharp straight edge (29).

7. An apparatus as claimed in claim 5, wherein the second upper electrode (27) has a free upper face (48) against which a syringe end piece (41) butts up axially, and a sharp straight edge (30) which is defined by this free upper face (48), and which can be applied radially against the outer surface of the needle (12) in order to establish tangential contact with this sharp straight edge (30).

8. An apparatus as claimed in claim 5, wherein at least one of the first and second upper electrodes (18, 27) is formed of an insert mounted in a detachable manner on an electrode support (19, 22).

9. An apparatus as claimed in claim 8, wherein the insert has several, in particular four, sharp straight edges (29, 30) and is mounted on the electrode support (19, 22) so as to make it possible to change the sharp straight edge (29, 30) designed to come into electrical contact with the outer surface of a needle (12).

10. An apparatus as claimed in claim 5, wherein at least one of the upper electrodes (18, 27) is made of tungsten carbide.

11. An apparatus as claimed in claim 5, wherein the first upper electrode (18) is mounted fixed with respect to a frame (1) of the apparatus and in that the second upper electrode (27) is mounted so that it can be displaced radially in translation between a position away from the first upper electrode (18) where only this first upper electrode is in contact with the outer surface of a needle (12) and a position close to the first upper electrode (18) where these two electrodes (18, 27) are in electrical contact with the outer surface of a needle (12).

12. An apparatus as claimed in claim 11, wherein the second upper electrode (27) is mounted securely in translation with a push button (4) adapted so that it can be actuated manually.

13. An apparatus as claimed in claim 5, wherein:

the axial distance between the lower electrode (15) and the electrical contact established between the outer surface of the needle (12) and the first upper electrode (18) is between 3 mm and 5 mm, the electric power source (2) comprises a voltage source delivering, between two terminals (34, 35) a continuous voltage comprised between 1.8 V and 2.5 V, the power circuit has a total internal resistance between the lower electrode (15) and the first upper electrode (18) via the electric power source (2), which is less than 50 mΩ, and the apparatus is portable.

14. An apparatus as claimed in claim 13, wherein the electric power source (2) comprises at least one pair of cells or accumulators, both cells or accumulators of the same pair being mounted in series, each cell or accumulator delivering a voltage of the order of 1.2 V.

15. An apparatus as claimed in claim 14, wherein the electric power source (2) comprises several pairs of cells or accumulators mounted in parallel, each cell or accumulator having a capacity above 1500 mAh.

16. The apparatus as claimed in claim 15, wherein the electric power source (2) comprises three pairs of cells or accumulators.

17. The apparatus as claimed in claim 15, wherein each cell or accumulator has a capacity of about 1800 mAH.

18. An apparatus as claimed in claim 14, wherein the electric power source (2) is formed of rechargeable cadmium-nickel accumulators.

19. The apparatus as claimed in claim 13, wherein the axial distance is 4 mm.

20. An apparatus as claimed in claim 13, wherein the power circuit includes at least one controlled electronic switching circuit (33) which makes it possible to supply or isolate at least one (15, 27) of the electrodes from the corresponding terminal (35) of the electric power source (2), and in that this controlled electronic switching circuit (33) is adapted so as to have an internal resistance, in the closed state where the electrode (15, 27) is supplied, which is less than 15 mΩ.

21. An apparatus as claimed in claim 20, wherein the controlled electrical switching circuit (33) includes an MOS transistor, and the apparatus includes a voltage booster circuit enabling the transistor to be polarized from the electric power source (2).

22. The apparatus as claimed in claim 20, wherein the controlled electronic switching circuit (33) has an internal resistance of about 10 mΩ.

23. An apparatus as claimed in claim 5, wherein it includes a secondary electronic circuit (38) making it possible in particular to control the operation of the apparatus, and wherein this secondary electronic circuit (38) includes an electrical supply circuit (39) with capacitor(s) connected to the electric power source (2), and adapted so as to supply the electronic components of the apparatus while the needle (12) is being melted.

* * * * *